United States Patent [19]

Carson

[11] Patent Number: 4,595,496

[45] Date of Patent: Jun. 17, 1986

[54] LIQUID COMPOSITION CONTROL

[75] Inventor: William W. Carson, Mendon, Mass.

[73] Assignee: Millipore Corporation, Bedford, Mass.

[21] Appl. No.: 763,743

[22] Filed: Aug. 8, 1985

Related U.S. Application Data

[63] Continuation-in-part of Ser. No. 625,931, Jun. 29, 1984, abandoned.

[51] Int. Cl.[4] .............................................. B01D 15/08
[52] U.S. Cl. .................................. 210/101; 210/198.2
[58] Field of Search ...................... 210/656, 198.2, 101

[56] References Cited

U.S. PATENT DOCUMENTS

| | | | |
|---|---|---|---|
| 3,398,689 | 8/1968 | Allington | 210/101 |
| 4,045,343 | 8/1977 | Achener et al. | 210/101 |
| 4,128,476 | 12/1978 | Rock | 210/101 |
| 4,347,131 | 8/1982 | Brownlee | 210/101 |
| 4,427,298 | 1/1984 | Fahy et al. | 366/132 |
| 4,437,812 | 3/1984 | Abu-Shumars | 210/198.2 |
| 4,448,692 | 5/1984 | Nakamoto et al. | 210/101 |
| 4,478,713 | 10/1984 | Girot et al. | 210/101 |

OTHER PUBLICATIONS

D. L. Saunders, "A Versatile Gradient Elution Device for HPLC", Journal of Chromatographic Science, Mar./Apr., 1977.

*Primary Examiner*—John Adee
*Attorney, Agent, or Firm*—Andrew T. Karnakis

[57] ABSTRACT

Apparatus for metering liquids in controlled proportions and for delivering the resultant mixture to a point of use. The disclosed apparatus is particularly suitable for use in liquid chromatography applications. In one embodiment a plurality of reservoirs each containing a liquid to be mixed are connected through respective hydraulic accumulators to a switching valve arrangement for modulating solvent composition to the inlet of a high pressure pump. A flow and composition controller sequentially activates each of the switching valves such that the non-uniformity associated with the pump draw stroke is effectively averaged over several cycles of switching valve actuation. Such averaging is accomplished by generating and maintaining a fixed relationship between switching valve cycles and pump cycles which ideally is expressed as a non-integer ratio. The accumulators permit the fluid flow to the pump inlet to respond more accurately to the switching valve actuations, particularly at high flow rates and short duration valve actuations.

10 Claims, 6 Drawing Figures

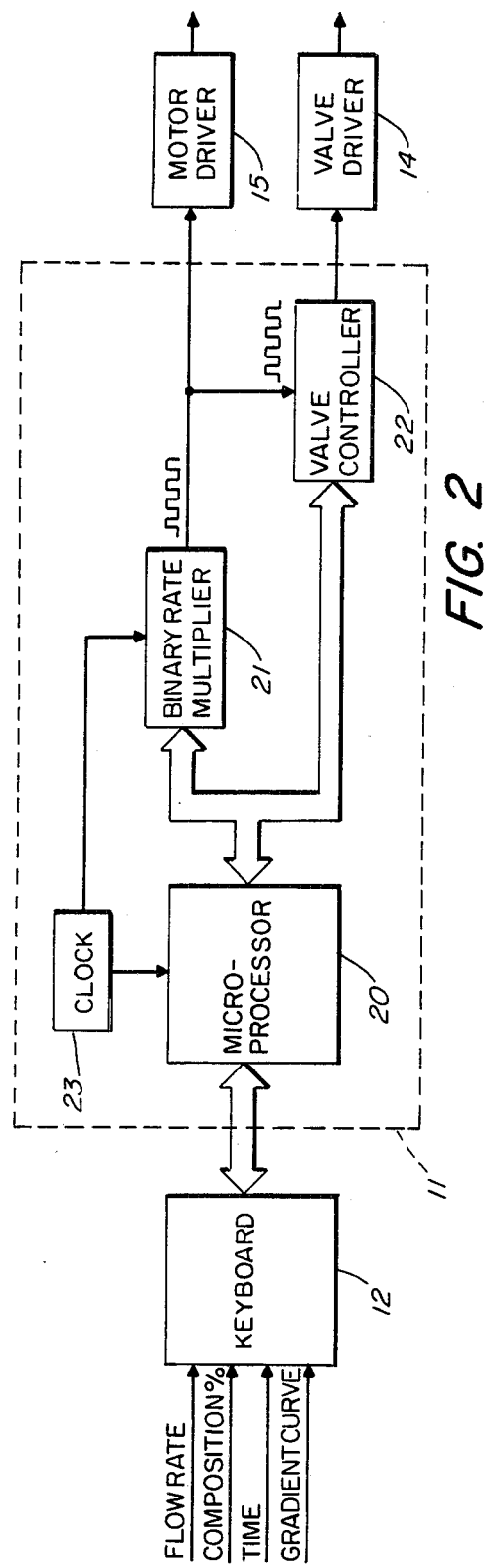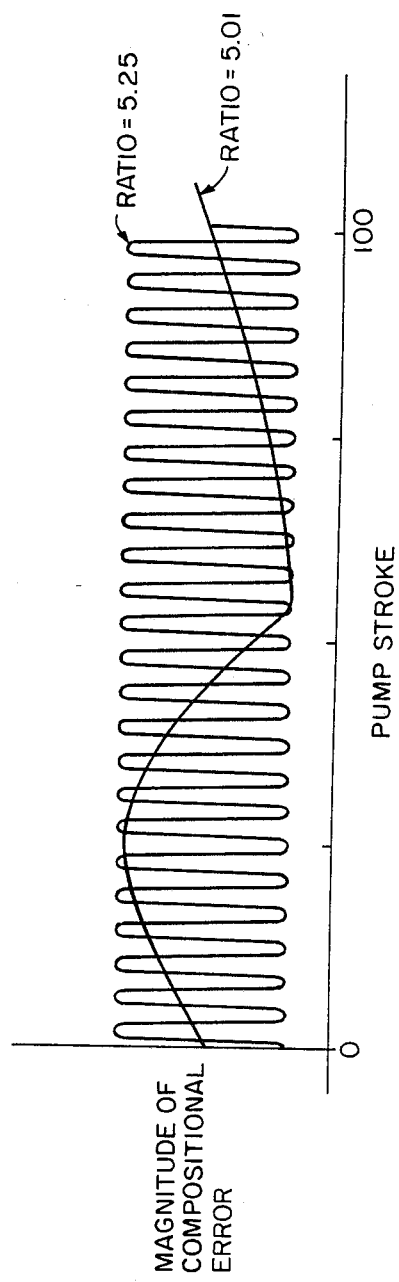

LIQUID COMPOSITION CONTROL

This is a continuation-in-part of copending application Ser. No. 625,931, filed June 29, 1984, now abandoned.

FIELD OF THE INVENTION

This invention relates generally to the mixing of liquids in controlled proportions. Specifically the invention relates to the production of a mixture of such liquids and the delivery of this mixture to a point of use. More particularly, the invention pertains to the ability to change the proportions of this mixture with time and to subsequently deliver the desired mixture over a range of flow rates in an accurate, repeatable manner that is suitable for use in liquid chromatography applications.

BACKGROUND OF THE INVENTION

There are many applications which require mixing liquids in controlled proportions. One such application is liquid chromatography wherein a liquid sample is passed by a flowing stream of liquid solvent (the mobile phase) through a column packed with particulate matter (the stationary phase). While passing through the column, the various components in the sample separate from one another by adsorbing and desorbing from the stationary phase at different rates such that these individual components elute from the column at different times. The separated components then flow through a detector which responds to each component both qualitatively and quantitatively, thereby providing information to the user about the constituents of the sample.

To achieve more effective separations, high performance liquid chromatography (HPLC) systems often use mixtures of solvents as the mobile phase. When this mixture is held constant, the system operates in an isocratic mode, whereas gradient chromatography is achieved when the components of the mixture are changed over time. The present invention has particular utility to both modes of operation.

Such mixtures of chromatographic solvents can be accomplished by having redundant high pressure pumps with each pump delivering its precise portion of liquid required to a mixing chamber downstream of the pump (i.e., high pressure side). However, these pumps are expensive, and the overall cost and complexity of the system is undesirably increased.

Alternatives have been proposed in the past to perform the desired metering at the low pressure side of the pump. Most often such systems include a plurality of reservoirs containing the liquids to be mixed, with each reservoir being suitably connected to the inlet of the pump. A valve arrangement between the reservoirs and the pump inlet meters each liquid in predetermined proportions. To meter the solvent volumes, the individual valves are sequentially actuated during the pump draw stroke. However, the draw stroke of the pump is non-uniformly related to the amount of liquid taken into the chamber. This is due to a combination of two effects—firstly, compressibility of both the liquid remaining in the chamber from the preceding delivery stroke and of certain internal pump components such as seals, which must first decompress before fresh liquid is taken in, and secondly, the non-uniform velocity of the piston during the draw stroke. Moreover, the long lengths of tubing from the solvent reservoirs to the switching valve arrangement create a hydraulic inertia that has detrimental effects during valve switching. Therefore, significant errors in the compositional mixture can result from these problems. Some of these errors vary over time and produce a compositional error that is detected as a "ripple" which interferes with the ability to detect and quantitate chromatographic peaks.

There have been many attempts to overcome the problems associated with these low pressure metering techniques, and much effort has been expended in attempting to produce accurate isocratic and gradient mixtures for HPLC mobile phases. Generally these attempts can be classified into three types—open loop averaging, open loop with compensation, and feedback. An example of the averaging technique is shown in U.S. Pat. No. 3,869,067 whose teaching is based on the premise that the desired composition is directly proportional to the actuation time of the individual valves in the system as a percentage of the total cycle time for actuation of all the valves. Since the rate at which fluid is drawn into the pump varies over time, simple time proportioning of valve actuation produces inaccurate, time varying compositions. To minimize these inaccuracies, the valves are actuated as frequently as possible so that the flow has not significantly changed between subsequent valve cycles. However, in this approach, the valve actuation times establish a limit on the frequency of actuation, particularly for lower percent composition values. Moreover, this technique still does not effectively address the non-uniform pump fluid draw stroke problem as large errors can occur if the valve cycle is in synchronism with the pump cycle.

U.S. Pat. No. 4,045,343 discloses a variation of the open loop averaging technique. The liquid composition is determined once again by the relative time each valve is opened in the cycle of actuation of all valves, but in this instance initiation of the switching valve cycle is delayed by a predetermined amount of pump stroke to correct for the non-uniformity due to compressibility during the pump draw stroke. However, the non-uniformity associated with pump draw stroke changes with different solvents and with differnt system back pressures so that the delay-factor compensation can only approximately compensate for the effect of such non-uniformity resulting in poor accuracy.

An example of the feedback type is shown in U.S. Pat. No. 4,128,476. Here a feedback error signal, which is derived from a measurement of system back pressure, is employed to alter the relative times each switching valve is opened during the pump draw stroke cycle. However, the measured parameter is indirectly related to composition, and moreover, this measurement is effected by external pressure influencing factors such as sample injections. Furthermore this feedback arrangement adds an overall degree of complexity and cost to the system that in certain applications is commercially undesirable.

Other attempts to minimize the interaction between valve cycles and pump cycles in a liquid chromatography multiple solvent delivering system are found in U.S. Pat. No. 4,427,298 and in an article by D. L. Saunders entitled, "A Versatile Gradient Elution Device for HPLC" (Journal of Chromatographic Science, Vol. 15, March/April 1977). Both of these references recognize that there are certain relationships between the pump cycle rate and the switching valve period that are to be avoided, namely values of valve cycle time which closely correspond to whole number multiples of the pump cycle time. However, neither reference is concerned with inaccuracies involved in such systems that are attributable to fluid inertia effects, particularly at high flow rates and also at short valve duration times.

It is apparent from the foregoing that the need exists for an accurate, reproducible technique for metering liquids in controlled proportions with minimum cost and complexity.

SUMMARY OF THE INVENTION

The present invention overcomes the foregoing limitations and disadvantages of the prior art by providing a system suitable for use in liquid chromatography applications. In accordance with a preferred embodiment of the invention, problems associated with the non-uniformity of the draw stroke of an HPLC pump and fluid inertia of the solvent delivery system are minimized with a concomitant minimal impact on system design and cost. This is accomplished by connecting a plurality of reservoirs, each containing a liquid to be mixed to form the mobile phase, through a switching valve arrangement to the inlet of a high pressure pump for ultimate delivery to the column. Directly adjacent to the switching valve arrangement on the side closest to the reservoirs are a series of hydraulic accumulators, one for each reservoir. A flow and composition controller actuates the switching valves in a manner that allows the non-uniformity to be equally shared by each of the liquid components over several cycles of switching valve actuation. A microprocessor drives both the pump and the fluid switching valves, and includes means for generating a ratio between the time to connect all of the reservoirs selected for actuation and the cycle time for a pump draw stroke. By connecting the output of the pump drive to the valve drive, this ratio is held constant throughout the operation of the chromatographic system within a given flow range. Ideally this is a non-integer ratio that can be either greater than or less than one. Judicious selection of this non-integer ratio controls the relative phasing between the switching valve cycle and pump draw stroke such that the beginning of each switching valve cycle occurs at a different point of the pump draw stroke, thereby providing a desired averaging of the intake non-uniformities and producing more accurate solvent mixtures. The accumulators allow the fluid flow through the valves to accurately correspond to the rate of volume displacement during the pump draw stroke. The non-integer ratio between valve cycle and pump cycle causes the valves to be actuated at widely varying pump intake rates. This fact coupled with the hydraulic inertia associated with the fluid in the tubing between the reservoirs and the valves results in inaccurate and unpredictable blended compositions. This is particularly significant at high flow rates and at short duration valve actuations and for systems designed to operate accurately over wide dynamic ranges of flow and composition. Another significant advantage of the invention is that compositional accuracy is substantially unaffected by changes in system back pressure and solvent compressibilities.

Other objects, advantages and aspects of the present invention will become apparent from the preferred embodiment when read in conjunction with the drawings.

DESCRIPTION OF THE DRAWINGS

FIG. 2 is a block diagram of the system of FIG. 1 showing details of the microprocessor generation and control of the desired ratio between switching valve cycle and pump draw stroke;

FIG. 4 is a graph of the magnitude and frequency of the envelope of compositional errors over 100 draw strokes for two preselected switching valve cycle to pump draw stroke ratios;

PREFERRED EMBODIMENT

Figure 1:
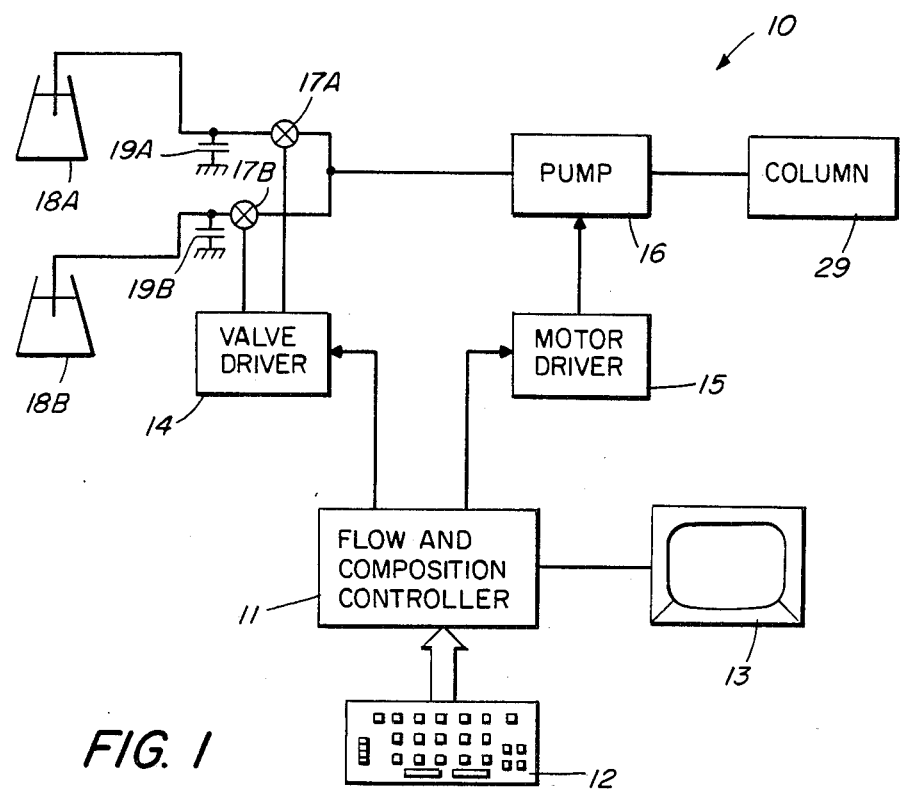
FIG. 1 is block diagram, partly in pictorial format, of the preferred embodiment.

FIG. 1 is an overall block diagram of a chromatographic system 10 built in accordance with the present invention. The system includes a flow and composition controller 11 that includes a microprocessor 20 (see FIG. 2), a keyboard 12 for loading parameters, and a cathode ray tube 13 (CRT) for displaying information. Also included is a valve driver 14 and a stepping motor driver 15 for operating a pump 16. The valve driver is connected to a pair of fluid switching valves 17A, 17B which are in turn connected by suitable tubing to respective liquid reservoirs 18A, 18B that hold the constituents of the mixture to be composed. Also shown are a pair of hydraulic accumulators 19A, 19B located between the reservoirs and the valves to minimize the effects of fluid inertia within the connecting tubing. The switching valves have a common output which is connected to the inlet port of the pump through a check valve 30 (see FIG. 3). The outlet port, also having a check valve 31, delivers the resultant mixture to a chromatographic column 29.

Under normal system operation the switching valves 17A, 17B are opened sequentially so that the pump 16 draws liquid from each of the reservoirs 18A, 18B. The composition of the liquid mixture will depend on the relative time each individual valve is opened to admit liquid from a particular reservoir as a percentage of the sum total of the actuation and delay times of the valves participating in the formation of the mixture; in this instance the combined actuation times of two valves. For purposes of this disclosure, the total elapsed time for the valve cycle to repeat, which is made up of actuation and delay times, is defined as the switching valve cycle time.

FIG. 2 shows further details of the system particularly the flow and composition controller 11. As mentioned, the controller includes the microprocessor 20, an Intel Model 8085, that provides the necessary command and control for the overall chromatographic system 10. A binary rate multiplier 21 sends a pulsed input to both the stepping motor driver 15 and a valve controller 22. A quartz clock 23 supplies the requisite timing for proper operation. Inputs made by the operator are entered through the keyboard 12 and include the flow rate of the pump 16, the desired composition of the liquid mixture expressed as a percentage of the amount of liquid desired from each of the reservoirs 18A, 18B, and the time characteristics and desired profile plot (i.e., gradient curve) if the gradient mode of operation is selected.

In order to illustrate the operation of the chromatograhic system 10 in accordance with the instant invention, assume for the present that an isocratic mixture of the two liquids in the reservoirs 18A, 18B is called for. The operator inputs the desired pump flow rate through the keyboard 12 to the microprocessor 20 which loads by known techniques a binary number corresponding to this input into the binary rate multiplier 21. The output of the binary rate multiplier is a pulse train representing the appropriate number and rate of motor steps required to drive the pump 16 at the called for speed to meet the desired flow rate. The pulse rate determines the pump cycle (i.e., defined as the beginning of one draw stroke to the beginning of the next draw stroke) since there are a known number of pulses in a pump cycle. In accordance with an important aspect of the invention, for a given flow rate range, a desired fixed relationship is created between switching valve cycles and pump cycles. This relationship is expressed as a ratio between two known quantities, i.e., the duration of the switching valve cycle expressed in motor steps and a pump cycle expréssed in motor steps. The number of pulses equal to a switching valve cycle for a given flow rate range is stored in memory, and upon command these pulses are then apportioned by the microprocessor between the two switching valves 17A, 17B to achieve the desired composition. From the desired volume fraction of each component of the mobile phase, the microprocessor generates a binary nubmer which expresses the volume fraction of that component as a fraction of the total number of pump steps in one switching valve cycle. These binary numbers are loaded into sequentially activated, decrementing counters within the valve controller 22, there being one such counter associated with each switching valve. While a counter is decrementing to zero, the valve associated with that counter remains open. Then the next counter decrements to zero while the first counter is reloaded.

Figure 3:
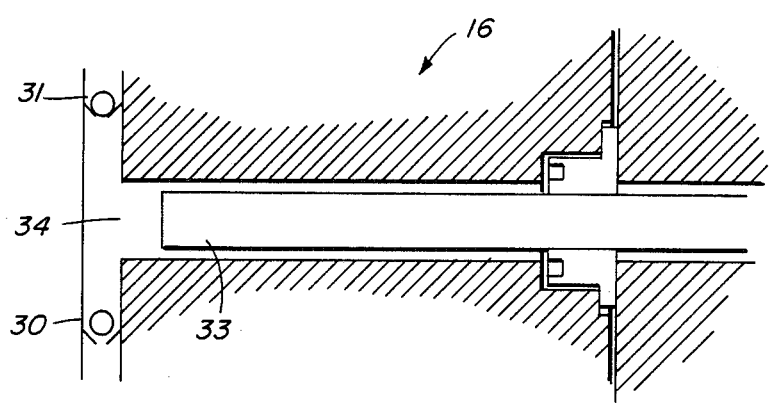
FIG. 3 is a schematic representation showing details of a typical HPLC pump.

Details of the relevant operation of the pump 16 are provided in FIG. 3. The pump is a dual chamber device whose reciprocating pistons operate in complementary fashion optimized to deliver fluid at a smooth and constant rate. This optimization for delivery smoothness causes large time-dependent variations of intake flow rates. Such pumps are commercially available from Waters Associates under Model No. M590. Considering for simplicity the movement of a single piston 33 within a pump chamber 34, FIG. 3 shows the piston position just after completion of the delivery stroke. The liquid refill cycle is commonly referred to as the pump draw stroke, and its beginnng is signified by the rearward movement of the piston. Such HPLC pumps do not expel all of the liquid in the chamber during the delivery stroke. Thus as the pump draw stroke begins, compression of this remaining liquid and of certain components within the pump such as seals occurs. Consequently no flow from the reservoirs 18A, 18B into the chamber 34 takes place initially. When the pressure conditions within the chamber allow the inlet check valve 30 to open, liquid begins to be drawn into the chamber. The point at which actual refill begins varies from chromatographic system to system and from application to application, being influenced by factors such as solvent composition, system back pressure and seal compliance. After the piston completes its draw stroke, it begins forward movement and the inlet check valve closes. As the pressure within the chamber rises above the system pressure the outlet check valve 31 opens and the liquid mixture, i.e., the mobile phase, is passed to the column 29.

The non-uniformity previously referred to relates to the amount of fresh fluid taken into the pump chamber during the draw stroke which varies from application to application. The variation of intake flow rate, due either to decompression of the pump head volume or to the non-uniformity of the piston velocity during the intake, creates problems in the accurate metering of liquids during the draw stroke cycle. Significant compositional errors in the liquid mixture will become apparent if the phase relationship of the pump draw stroke and switching valve cycle remain constant during system operation.

To avoid the problems associated with the non-uniformity of the volumetric intake rate, it has been found advantageous to establish the relationship between the pump cycle time and the switching valve cycle time as a non-integer ratio that can be either greater than or less than one. In this manner the relative phasing between the switching valve cycle and the pump draw stroke is such that the beginning of each switching valve cycle occurs at a different point in the pump draw stroke. This has the effect of sequential valve cycles sampling different portions of the cyclic non-uniformity of the intake flow, thereby averaging the non-uniformity over many switching valve cycles. In other words, each successive switching valve cycle would be displaced relative to the draw pump stroke position by a known amount resulting in a compositional averaging which produces a more accurate mixture after several draw strokes. The selection of this non-integer ratio is determined in accordance with criteria to be discussed subsequently.

The adoption of this non-integer ratio relationship between valve cycle and pump cycle creates other concerns with respect to compositional accuracy resulting from the valves being actuated at widely varying pump intake rates. In particular, switching a valve open or closed during the rapid intake portion of the pump draw stroke attempts to cause instantaneous changes in flow through the valve. The hydraulic inertia associated with the fluid in the relatively long length of tubing between the solvent reservoir and the valve resists these instantaneous flow changes. This results in inaccurate and unpredictable compositions which are highly dependent on specific operating conditions such as flow rate, tubing length, tubing diameter, tubing stiffness, solvent density, solvent compressibility, etc. These problems become magnified at a high flow rate and/or short duration valve actuations, particularly in systems designed to operate over wide dynamic ranges of flow rate and solvent composition.

Figure 5:
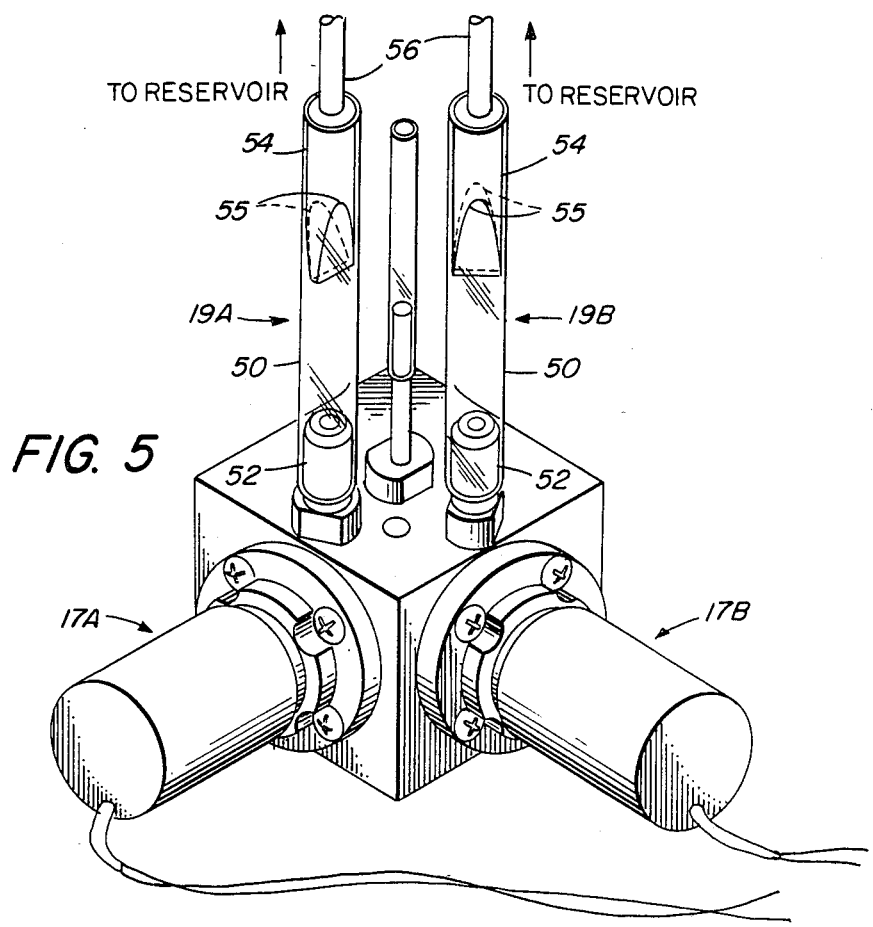
FIG. 5 is a perspective view of the valve switching arrangement showing the location of the preferred accumulators in accordance with the embodiment of FIG. 1.
Figure 6:
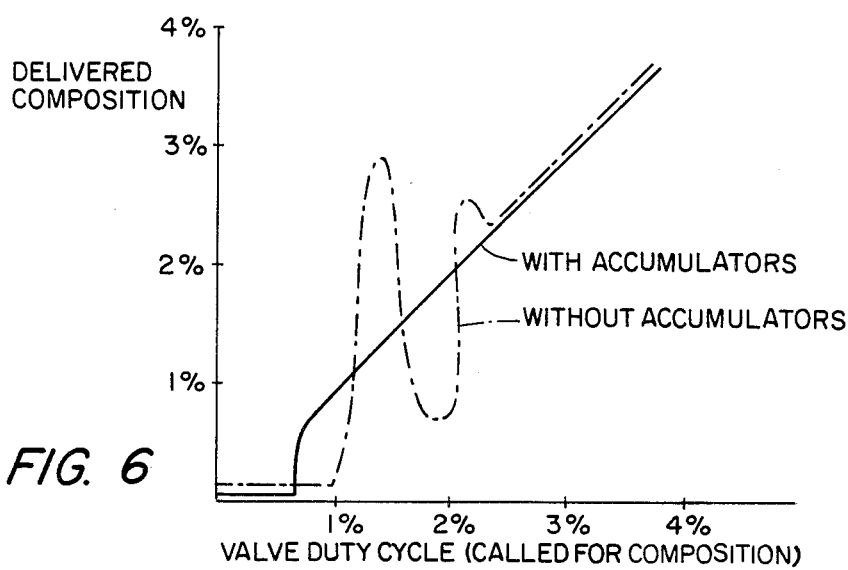
FIG. 6 is a graph comparing the effect of valve duty cycle on delivered composition with and without accumulators.

FIG. 5 shows the accumulators 19A, 19B located directly adjacent the switching valves 17A, 17B, on the side closest to the reservoirs 18A, 18B that are used to overcome the difficulties associated with the above-described hydraulic inertia effects. Each accumulator consists of a soft-walled, flexible plastic tube 50 of generally circular cross-section. The tube 50 is adapted to snugly slide over rigid plastic connecting tubes 52, 54 with the connecting tube 54 holding the relatively long length of flow tubing 56 that connects with the reservoirs. The end of the tube 50 adjacent the connecting tube 54 is caused to assume approximately the cross-section of a flattened elipse as indicated by the reference numeral 55. This flat segment allows a significant internal volume change in the tube 50 to occur with little change in pressure thereby allowing the accumulator to overcome the effects of hydraulic inertia. FIG. 6 shows the dramatic improvement in delivered compositional accuracy with the use of the accumulator (and correspondingly the gross inaccuracies without the accumulator). As mentioned, these problems intensify as the valve actuation time is reduced or at high flow rates.

Returning to a discussion of the non-integer ratio, in one particular embodiment, the desired ratio was selected as 5.25 switching valves cycles for every pump cycle, where 1280 motor advances defines a pump cycle, resulting in a switching valve cycle duration of 244 motor advances. Stated another way, if the first switching valve cycle begins synchronously with the pump cycle, i.e., at motor step 1, the first switching valve will turn on in ensuing cycles at motor steps 245, 489, etc. From the principles discussed above, if, for example, a 50—50 mixture is desired the first switching valve will turn off at approximately motor step 122 while the second switching valve will be actuated from motor step 123 to motor step 244.

In accordance with an important aspect of the invention, the ratio between pump cycle time and switching valve cycle time is held constant over a range of flow rates. In the embodiment being described, this is achieved by supplying the pulse train generated at the output of the binary rate multiplier 21 to the valve controller 22. This hardwired connection forces the switching valves 17A, 17B to time themselves in proportion to pump cycle time which represents inverse motor speed. If the flow rate is halved, for example, then the valve cycle time is doubled to make the ratio remain constant. Although the ratio is precise in isocratic operation, during gradient operation which calls for composition mixtures to be changing over time, minor, insubstantial deviations in the ratio will occur depending on choice of measurement period and phase relation with the switching valves.

The actual determination of a desirable ratio depends on the chromatographic application, the particular characteristic of the pump draw stroke for the liquids being delivered, the accuracy desired, acceptable delay volume for mixing, acceptable composition ripple, and certain hardware limitations, most notably the on-off cycle time of the switching valves. Integer ratios are not desirable because they lead to synchronism between the pump draw stroke and the switching valve cycle resulting in poor accuracy. Synchronous valving causes the fluid metering to be vulnerable to effects which are synchronous with piston displacement, notably head decompression and non-uniform intake as detailed above. As has been mentioned, it is not possible to achieve fast enough valve switching, especially when low percentage liquid compositions (e.g., 1%) are called for, to overcome the undesirable effects of synchronism.

Non-integer ratios provide generally results because of the displacement of the start of each successive switching valve cycle with respect to the pump draw stroke. Because of the constantly shifting phase relationship between switching valve cycles and pump stroke cycles, undesirable effects which are in phase with the pump stroke are exerted approximately equally over the actuation periods of all valves used in generating a mixture. Thus, on average, the delivery of all components of the mixture are augmented or decremented by the same percentage. Hence the composition of the mixture produced by the switching valve and pump arrangement is essentially unaffected by changes in system back pressure and solvent composition.

Regarding ratio optimization, it is apparent that changes to the fractional portion of the non-integer ratio can improve the compositional accuracy of the delivered mixture by varying the increment of phase shift with each pump stroke, thereby determining how slowly or rapidly the switching valve cycles shift with respect to pump stroke cycles.

Assume that a ratio is selected which is only slightly removed from an integer ratio; e.g., 5.01 switching valve cycles per pump stroke cycle. The 0.01 remainder causes a phase shifting of the valve cycling with respect to pump cycling which increments by 0.01 valve cycles for each pump stroke. After 100 pump strokes, one complete valve cycle of phase shift will have been accomplished, and the initial or starting phase relationship will be recovered. As is shown in FIG. 4, the use of such a small phase increment produces a composition output characterized by approximate similarity of the mixture delivered in adjacent pump strokes, but with a long-term compositional ripple coherent with the 100 pump stroke period before repetition of the initial phase relationship. While a mixing device could be employed downstream of the pump to compositionally average the solvent delivered over this 100 stroke period to produce a smooth output, the averaging volume would be so large with respect to accepted chromatographic instrumentation and practices that it would seriously distort or eliminate intentional compositional changes required for gradient elution and initial condition equilibration, thereby rendering the instrument ineffective. In practice mixing volumes should be a small fraction of the total chromatographic run volume, less than 0.2, and preferably less than 0.05.

For the above reasons, non-integer ratios producing larger increments of phase shift per pump stroke are desirable. An example is the ratio 5.25 to 1 which generates a 244 step duration switching valve cycle in a 1280 step pump stroke cycle. The fractional cycle residual from each pump stroke creates a 60 step offset or phase change increment in valve cycle timing with each successive pump stroke. Because the fraction 60/244 is very nearly equal to $\frac{1}{4}$, it is apparent that there is a near repetition of phase relationship after 4 pump stroke cycles, while a true and precise repetition is obtained only after 244 pump strokes. The following benefits as illustrated in FIG. 4 results from selecting this ratio. It should be noted that, for illustrative simplicity, whereas FIG. 4 shows a continuous envelope of composition versus valve cycle phase at the start of a pump stroke, in actuality the composition consists of one discrete composition error value for each start of pump stroke. First, the four pump stroke periodicity permits more accurate composition when measured over 4 strokes. The compositional ripple has a sufficiently short period in the volume domain (4 pump strokes) to be adequately compositionally averaged within a mixing volume appropriate for chromatographic gradient elution.

To illustrate the practical application of the aforementioned discussion, the number of switching valve cycles within a pump draw stroke is limited to ten for mixtures and flow rates generally used in chromatographic systems. Since a typical minimum reliable switching valve actuation time is twenty milliseconds, and the high performance chromatographic pump of the present embodiment displaces 0.225 milliliters per stroke, then a 1% called for mixture at 1 milliliters per minute flow would require 4.4 pump strokes per minute, or one each 13 seconds. The valve associated with the 1% component must be opened for 1/100 of 13 seconds or approximately 130 milliseconds, so at 20 milliseconds minimum reliable valve open time, a maximum of six valve cycles could be accommodated. A fluid volume sufficient to homogenize the composition of four successive pump strokes is acceptable for typical chromatography applications. Thus the selection of a ratio of 5.25 would be ideally suited to this type of system.

As mentioned there are several factors to consider when selecting a proper ratio. However, the guidelines and examples presented above would allow one of ordinary skill in the design of liquid chromatographic systems to select a ratio that is ideal for his or her particular needs.

Although a preferred embodiment has been set forth in detail above, this is solely for the purpose of illustration as numerous modifications may become apparent to those of skill in the art. For example, the system has been described as operating under the command of a digital computer, but the principles of the invention can be extending to analog circuitry as well. Furthermore the preferred embodiment describes a hardwired connection between the binary rate multiplier and the valve controller as controlling the sequencing of the switching valves to be in concert with the motor speed. However, as is well known this control can be achieved by programmed instructions resident within the microprocessor or by a mechanical means such as a gear train driven by the pump motor and operating the valves. Additionally, generation and maintenance of accurate mixing of a plurality of liquids has been shown as functioning in a gradient mode of chromatographic operation, but the principles illustrated can be adapted to perform flow rate programming, that is varying over time the mixture flow rate instead of its composition to achieve the desired chromatographic separations. Therefore the invention is to be construed in light of the foregoing and the appended claims.

I claim:

1. A liquid chromatography system comprising:
a column;
a plurality of reservoirs each containing a liquid to be mixed together to form a mobile phase;
a pump having an inlet and an outlet;
a plurality of flow conduits for connecting each of said reservoirs to the inlet of said pump for delivery over a range of flow rates to said column;
valve means interposed between each of said reservoirs and said pump inlet;
means for selectively activating each of said valve means to admit liquid from each of said reservoirs into said pump inlet, the total actuation time for each valve means participating in the formation of the mixture defining a switching valve cycle time, and the proportion of the time each of said valve means is activated to said switching valve cycle time defining the composition of the resulting mixture;
means for generating a ratio of said switching valve cycle time to the cycle time of said pump, said ratio being a non-integer; and
accumulator means associated with each of said reservoirs and located between said reservoirs and said valve means to permit the fluid flow through said valve means to accurately correspond to the rate of fluid volume displacement during the inlet draw stroke of said pump.

2. Apparatus as claimed in claim 1 wherein said non-integer ratio is greater than one.

3. Apparatus as claimed in claim 1 wherein said non-integer ratio is less than one.

4. Apparatus as claimed in claim 1 wherein the increment of phase shift between switching valve cycles and pump cycles produced by said non-integer ratio is sufficiently large to produce an approximate periodic compositional inaccuracy whose period is less than 0.2 of a chromatographic gradient elution period.

5. Apparatus as claimed in claim 1 wherein the increment of phase shift between switching valve cycles and pump cycles produced by said non-integer ratio is sufficiently large to produce an approximate periodic compositional inaccuracy whose period is less than 0.05 of a chromatographic gradient elution period.

6. Apparatus as claimed in claim 1 wherein said activating means comprises digital computer means, said computer means producing an output signal for driving said pump in response to inputs supplied through computer-operator interface means.

7. Apparatus as claimed in claim 6 further comprising signal generating means for supplying an output signal to drive said pump at a desired flow rate and valve controller means for controlling the actuation of each of said valve means, said output signal being supplied to the input of said valve controller means whereby said ratio is maintained substantially constant with changes in either the pump cycle time or in said mixture composition over said range of flow rates.

8. Apparatus as claimed in claim 1 wherein said accumulator means is located directly adjacent to said valve means.

9. Apparatus as claimed in claim 1 wherein said accumulator means comprises a soft-walled, flexible plastic tube.

10. Apparatus as claimed in claim 9 wherein said tube includes a flattened segment thereby allowing said accumulator means to undergo a significant internal volume change with little change in pressure.

* * * * *